(12) United States Patent
Lang

(10) Patent No.: US 8,649,867 B2
(45) Date of Patent: Feb. 11, 2014

(54) PATIENT DEVICE FOR WIRELESS DATA COMMUNICATION WITH AN IMPLANT

(75) Inventor: Martin Lang, Weisendorf (DE)

(73) Assignee: Biotronik CRM Patent AG, Baar (CH)

( * ) Notice: Subject to any disclaimer, the term of this patent is extended or adjusted under 35 U.S.C. 154(b) by 309 days.

(21) Appl. No.: 11/940,798

(22) Filed: Nov. 15, 2007

(65) Prior Publication Data

US 2008/0172110 A1 Jul. 17, 2008

(30) Foreign Application Priority Data

Jan. 11, 2007 (DE) .......................... 10 2007 001 705

(51) Int. Cl.
*A61N 1/02* (2006.01)

(52) U.S. Cl.
USPC ............................................... 607/32; 607/60

(58) Field of Classification Search
USPC ............................................... 607/30–33, 60
See application file for complete search history.

(56) References Cited

U.S. PATENT DOCUMENTS

| | | | |
|---|---|---|---|
| 6,477,424 B1 | 11/2002 | Thompson et al. | |
| 2004/0122295 A1 | 6/2004 | Hatlestad et al. | |
| 2006/0212092 A1* | 9/2006 | Pless et al. | ....................... 607/45 |

FOREIGN PATENT DOCUMENTS

| | | |
|---|---|---|
| DE | 199 30 263 | 12/2000 |
| EP | 1 310 272 | 5/2003 |
| EP | 1310272 | 5/2003 |
| WO | 03066159 | 8/2003 |
| WO | WO 03/066159 | 8/2003 |

OTHER PUBLICATIONS

European Search Report, dated Apr. 14, 2008.
German Search Report, dated Sep. 18, 2007.

* cited by examiner

*Primary Examiner* — Scott Getzow
(74) *Attorney, Agent, or Firm* — ARC IP Law, PC; Joseph J. Mayo

(57) ABSTRACT

A patient device (10) having a first interface (20) for the wireless transmission of data from and to an implant and having a second interface (22) for the remote data communication with a central service center and having a third interface (24) different from the first and second interfaces, the third interface (24) being implemented for connecting a programming device to the patient device (10) and the patient device (10) being implemented to relay programming data received via the third interface (24) on the part of a programming device to the first interface (20) and wirelessly transmit it to an implant.

12 Claims, 2 Drawing Sheets

PATIENT DEVICE FOR WIRELESS DATA COMMUNICATION WITH AN IMPLANT

This application takes priority from German Patent Application DE 10 2007 001 705.9, filed 11 Jan. 2007, the specification of which is hereby incorporated herein by reference.

BACKGROUND OF THE INVENTION

1. Field of the Invention

The present invention relates to a patient device which has a wireless, bidirectional interface for the bidirectional transmission of data between the patient device and an implant such as a cardiac pacemaker, implantable cardioverter/defibrillator (ICD), or the like. In addition, the patient device has a second interface for remote data communication with a central service center.

2. Description of the Related Art

Patient devices of this type are fundamentally known in various forms and allow a cardiac pacemaker or defibrillator patient to be monitored in regard to the function of the implant or the physiological data detected by the implant even outside a doctor's office or a hospital. Modern implants of the cited type, implantable cardiac pacemakers or implantable cardioverters/defibrillators, are capable of detecting manifold physiological data which provides information about the development of the particular (cardiac) illness of the patient. On this basis, the particular implant may provide the particular best possible treatment for the patient independently or after corrective and/or programming intervention of the physician. The data detected on the part of the implant includes, for example, intracardial electrocardiograms, which may be transmitted remotely with the aid of a corresponding implant and the associated patient device to a central service center and analyzed by a physician there or made available to a physician for analysis from there. Other data which may be transmitted from the implant to the service center is operational data of the implant such as its battery status or the like, for example. To transmit this data, the patient device has a first, implant-side interface on one hand, which is implemented having a transceiver for communication with a corresponding interface of the implant. In addition, the patient device has a second interface for the remote data communication with the service center. In the simplest case, this second interface is a telephone modem. Known alternatives are, for example, all conceivable variants of an Internet connection or a data link via a mobile wireless network.

Programming the implant via the two above-mentioned interfaces of the patient device has already been considered in the prior art. The possibility of remote programming of the implant via the patient device from the service center results in this way. The cited remote programming of the implant via a service center has not been successful up to this point, probably because in this conceivable variant, firstly technical problems result, such as the question of data security and integrity, but also because, if an implant is remotely programmed by the service center, an attending physician, who may immediately engage to help in case of doubt, is typically not on location at the patient.

A currently typical scenario therefore appears as follows: For example, an intracardial ECG which represents a critical state of the patient, or operational data of the implant which requires urgent handling, is received in the central service center. In this case, the physician attending the particular patient is immediately informed by the service center and may summon the affected patient to him or visit him personally. The physician may then perform further diagnoses in direct proximity to the patient and perform possibly required further queries on the implant or reprogramming of the implant with the aid of a typical programming device. The data communication between programming device and implant also occurs wirelessly, but via another, essentially shorter-range inductive data link between implant and a programming head of the programming device. This programming head of the programming device must be brought in direct proximity to the implant and typically laid directly on the skin of the patient for the data communication with the implant. The advantage of a short-range data communication of this type is that the danger of interference and malfunctions of the data transmission link is quite low. Because the proximity of a physician is desirable in any case in most cases, the requirement of the proximity of a physician also does not appear to be a disadvantage.

Nonetheless, the need exists to improve the scenario corresponding to the prior art, without having to accept the disadvantages of the suggested alternatives.

BRIEF SUMMARY OF THE INVENTION

For this purpose, a patient device is suggested according to the present invention which, in addition to the two cited interfaces, has a third interface, which is implemented to connect a—preferably typical—programming device. The patient device is in turn implemented to relay programming data received via the third interface on the part of the programming device to the first (wireless) interface for communication with the implant and to transmit it wirelessly to an implant.

In this way, the patient device may replace the typical programming head of a programming device, and the second data communication interface for wireless data communication with the programming head may be saved in the implant. At the same time, the complete functionality of the programming device is always available to the physician. Because the patient device is designed in such a way that it is quasi-transparent to the data exchange between programming device and implant, i.e., it permits the data exchange in both directions unobstructed and without altering the data, the compatibility between programming device and implant is entirely preserved and there is no functional restriction when dealing with the programming device. The advantage of a relatively short-range telemetry between patient device and implant and the advantages in regard to the security from interference are preserved.

Alternatively, wireless interfaces, such as Bluetooth, or wired interfaces, such as USB, or also an interface on the patient device, which corresponds to the typical interface between programming device and programming head, suggest themselves as the preferred interface between patient device and programming device.

In regard to the implant-side interface of the patient device, it is advantageous if this interface is not integrated in the patient device itself, but rather in a relatively smaller handset or mobile part, which is preferably not larger than the palm of a hand and which makes it easy to produce a small distance to the implant using the mobile part, to increase the transmission reliability once again in this way. The patient device itself is also typically portable and mobile in this meaning. However, it is normally more voluminous than the suggested mobile part. The mobile part is preferably connected via a wired connection to the base part of the patient device.

In regard to the internal construction of the patient device and/or the base part of the patient device, inter alia, two alternatives suggest themselves. On one hand, the third interface for the connection of the programming device may be connected directly and immediately to the first, wireless interface for the data communication with the implant. In this way, the desired transparency of the programming device is implemented most effectively in the hardware as well. "Directly" in this context means that no components of the patient device which could potentially alter data are situated between the first and third interfaces. "Immediately" in this context means that the data does not experience any delay, e.g., through buffer memories, between the first and third interfaces.

On the other hand, the third interface for connecting the programming device may also be connected to a central control unit of the patient device, which is in turn also connected to the first and second interfaces of the patient device. In this case, the central control unit, as a potentially data-altering and potentially data-delaying component of the patient device, is designed in such a way that it relays programming commands of the programming device and data from the implant to the programming device without unnecessary alteration or delay.

To allow the typical remote monitoring by a central service center with the aid of the patient device, it preferably has a data memory which is connected to the central control unit of the patient device and allows it to receive data on the part of the implant independently of whether the remote data transmission at the service center is currently available. Data of the implant may then be buffered in the memory of the patient device and transmitted when a connection is available for the remote data communication with the central service center. The latter may be the case only once a day at specific times, for example, while a data communication between implant and patient device is also to occur multiple times per day.

A patient device of the type according to the present invention thus allows the three following operating scenarios equally:

Firstly, the typical remote monitoring operation is possible, in which the data transmission between implant and patient device on one hand and the remote data transmission between patient device and central service center on the other hand occur at different times using buffering of the particular transmitted data in a memory of the patient device.

In addition, a patient device of the type according to the present invention allows programming of the implant to be performed even from the remote, central service center, as has already been suggested in the prior art.

Finally, the patient device according to the present invention simplifies the programming of the implant and the communication with the implant with the aid of a programming device, for which the patient device practically assumes the function of a programming head.

BRIEF DESCRIPTION OF THE DRAWINGS

In this meaning, the present invention will be explained in greater detail on the basis of exemplary embodiments with reference to the figures. In the figures.

DETAILED DESCRIPTION OF THE INVENTION

Further advantages and features of the programming device according to the present invention result from the following description of exemplary embodiments.

Figure 1:
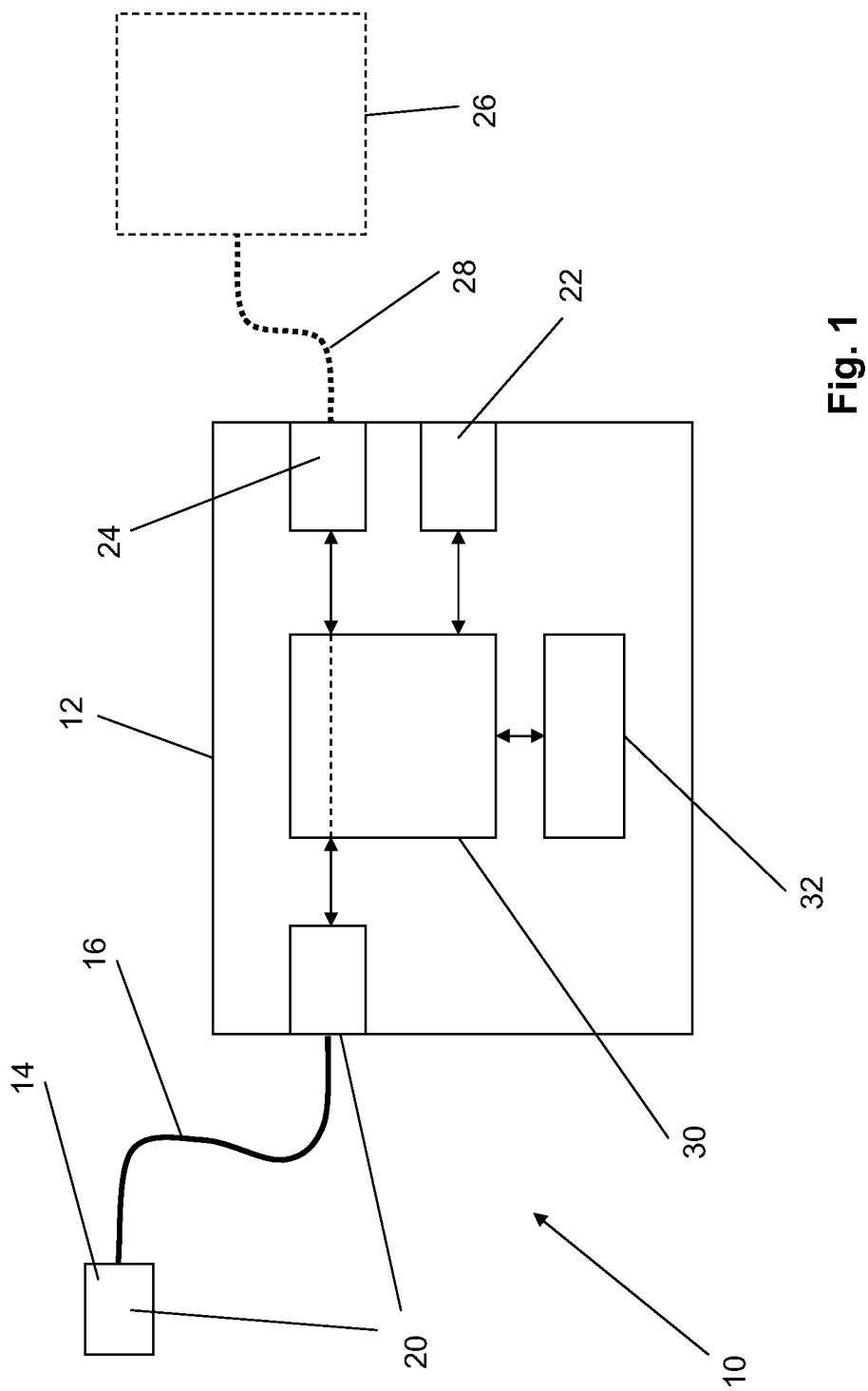
FIG. 1: shows a first variant of a programming device according to the present invention.

A patient device 10 according to the present invention, which has a mobile base part 12 and a mobile part 14, which is connected via a cable 16 to the mobile base part, is shown in FIG. 1.

The mobile part 14 is approximately the size of the palm of a hand and is thus significantly smaller than the base part 12. The base part 12 may be approximately the size of a desk telephone, for example.

The patient device 10 has three interfaces, namely a first interface 20 for the wireless transmission of data from and to an implant. The first interface 20 is present twice in the patient device 10, namely on one hand in the base part 12 and on the other hand in the mobile part 14. The mobile part 14 thus replicates the first interface 20 of the patient device 10.

Furthermore, a second interface 22 is provided for the remote data communication with a central service center. This second interface may be a telephone modem, for example, or any other type of interface which permits remote data transmission via the Internet, for example.

Finally, the patient device 10 has a third interface 24, which is used for connecting a programming device 26, which is illustrated by dashed lines in FIG. 1. The programming device 26 is connected via a cable 28 to the patient device 10 in the example shown in FIG. 1. Alternatively, the third interface 24 may also be implemented as a Bluetooth transceiver, to be able to communicate wirelessly with the programming device 26.

The patient device 10 has a central control unit 30 in the base part 12, which is connected to all three interfaces 20, 22, and 24 and, in addition, is connected to a memory 32.

The patient device 10 may thus be used in a typical way for remote monitoring of an implant. For this purpose, the implant regularly transmits data to the first interface 20. The data is stored in the memory 32 of the patient device 10 and may be retrieved at a later time from the central service center. For this purpose, the central service center establishes a remote data link to the patient device 10 via the second interface 20.

In addition, as in typical patient devices, the possibility is provided that an implant is remotely programmed from the central service center. In this case, the data transmission occurs from the central service center to the implant with the patient device 10 as a relay station and both interfaces, namely the first interface and the second interface 22, are active simultaneously. In the same way, an immediate data query of implant questions may be performed by the central service center.

In addition, the patient device 10 opens up the new possibility of connecting a programming device such as the programming device 26 to the patient device 10 and to perform programming of an implant via the first interface 20 with the aid of the programming device 26. For this purpose, the programming device 26 is connected to the third interface 24 of the patient device 10. The patient device 10 is implemented in such a way that the programming device 26 has a transparent or also an actually direct data access to the first interface 20 in this case and may thus transmit data from and to the implant via this interface. To obtain the greatest possible security from interference for this purpose, in contrast to known patient devices, in the patient device 10, the mobile part 14 is provided, which houses a transceiver for the first interface 20 and, if necessary, may be brought into the immediate proximity of the implant, so that de facto only a short wireless transmission link has to be operated without interference between implant and mobile part 14. If the patient device 10 is implemented as sufficiently compact and movable, the mobile part 14 may also be dispensed with. The exemplary embodiments in FIG. 1 and FIG. 2 only differ in how the third interface 24 for the connection of the programming device 26 is connected to the first interface 20 for the wireless data transmission from and to the implant.

In the embodiment variant shown in FIG. 1, the data link between the third and first interfaces is conducted transparently via the central control unit 30.

Figure 2:
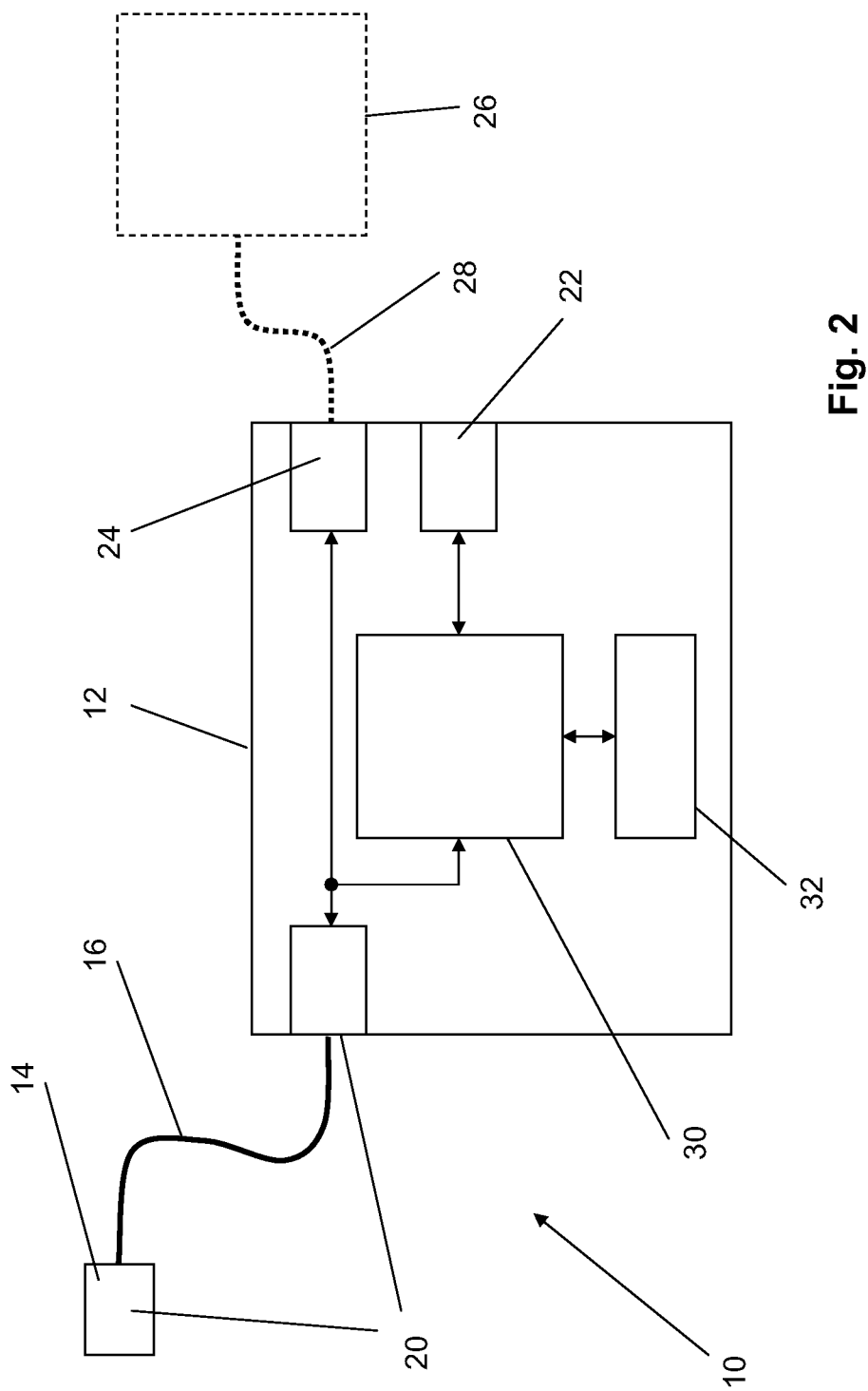
FIG. 2: shows a second variant of a programming device according to the present invention.

In the embodiment variant shown FIG. 2, the link is implemented directly between the third interface 24 and the first interface 20.

What is claimed is:

1. A patient device (10) comprising:
   a first interface (20) within said patient device configured to wirelessly communicate with an implant;
   a second interface (22) within said patient device configured to remotely communicate with a central service center;
   a programming device interface (24) within said patient device, specifically configured to communicate with a programming device, wherein said programming device interface is different from the first and second interfaces wherein said programming device interface (24) is configured to connect said programming device to said patient device (10), and wherein said patient device (10) is configured to transparently or directly relay programming data received via said programming device interface (24) from said programming device to said first interface (20) and wherein said first interface (20) is configured to transmit said programming data wirelessly to and from said implant via said first interface;
   wherein said first interface is the only interface that communicates with said implant and wherein said second interface and said programming device interface both communicate with said implant via said first interface; and,
   wherein said patient device is configured to enable simultaneous communication over said programming device interface and said second interface.

2. The patient device according to claim 1, wherein said programming device interface (24) is implemented as a wired interface configured to connect with a programming device via a cable.

3. The patient device according to claim 1, wherein said programming device interface (24) is implemented as a wireless interface for wireless transmission from and to a programming device.

4. The patient device according to claim 1 further comprising a mobile base part (12) and a mobile part (14) connected to said base part (12) via a wireless or a wired data link, which is smaller than said base part (12) and houses said first interface (20) or has an interface corresponding to said first interface (20).

5. The patient device according to claim 4, wherein said mobile part (14) is connected via a cable connection (16) to said base part (12).

6. The patient device according to claim 1 wherein said programming device interface (24) is connected directly to said first interface (20) in such a way that no alteration of transmitted data occurs between said programming device interface (24) and said first interface (20).

7. The patient device according to claim 6, wherein said programming device interface (24) is connected immediately to said first interface (20) in such a way that data does not experience any delay between said programming device interface (24) and said first interface (20) or vice versa.

8. A patient device (10) comprising:
   a first interface (20) within said patient device configured to wirelessly communicate with an implant;
   a second interface (22) within said patient device configured to remotely communicate with a central service center;
   a programming device interface (24) within said patient device, specifically configured to communicate with a programming device, wherein said programming device interface is different from the first and second interfaces wherein said programming device interface (24) is configured to connect said programming device to said patient device (10), and wherein said patient device (10) is configured to transparently or directly relay programming data received via said programming device interface (24) from said programming device to said first interface (20) and wherein said first interface (20) is configured to transmit said programming data wirelessly to and from said implant via said first interface;
   a mobile base part (12);
   a mobile part (14) connected to said mobile base part (12) wherein said mobile part (14) is smaller than said base part (12) and houses said first interface (20);
   wherein said first interface is the only interface that communicates with said implant and wherein said second interface and said programming device interface both communicate with said implant via said first interface on said mobile part (14); and,
   wherein said patient device is configured to enable simultaneous communication over said programming device interface and said second interface.

9. The patient device according to claim 8, wherein said mobile part (14) is connected via a cable connection (16) to said base part (12).

10. The patient device according to claim 8 wherein said programming device interface (24) is connected directly to said first interface (20) in such a way that no alteration of transmitted data occurs between said programming device interface (24) and said first interface (20).

11. The patient device according to claim 10, wherein said programming device interface (24) is connected immediately to said first interface (20) in such a way that data does not experience any delay between said programming device interface (24) and said first interface (20) or vice versa.

12. A patient device (10) comprising:
   a first interface (20) within said patient device configured to wirelessly communicate with an implant;
   a second interface (22) within said patient device configured to remotely communicate with a central service center;
   a programming device interface (24) within said patient device, specifically configured to communicate with a programming device, wherein said programming device interface is different from the first and second interfaces wherein said programming device interface (24) is configured to connect said programming device to said patient device (10), and wherein said patient device (10) is configured to transparently or directly relay programming data received via said programming device interface (24) from said programming device to said first interface (20) and wherein said first interface (20) is configured to transmit said programming data wirelessly to and from said implant via said first interface;
   a mobile base part (12);
   a mobile part (14) connected to said mobile base part (12) wherein said mobile part (14) is smaller than said base part (12) and houses said first interface (20);

wherein said first interface is the only interface that communicates with said implant and wherein said second interface and said programming device interface both communicate with said implant via said first interface on said mobile part (14);

wherein said programming device interface (24) is connected directly to said first interface (20) in such a way that no alteration of transmitted data occurs between said programming device interface (24) and said first interface (20) and wherein said programming device interface (24) is connected immediately to said first interface (20) in such a way that data does not experience any delay between said programming device interface (24) and said first interface (20) or vice versa; and, wherein said patient device is configured to enable simultaneous communication over said programming device interface and said second interface.

\* \* \* \* \*